(12) United States Patent
Ruggiero et al.

(10) Patent No.: US 12,029,711 B1
(45) Date of Patent: Jul. 9, 2024

(54) DOSAGE FORMS OF MIRDAMETINIB

(71) Applicant: SpringWorks Therapeutics, Inc., Stamford, CT (US)

(72) Inventors: Piero L. Ruggiero, Stamford, CT (US); Kristin Patterson, Stamford, CT (US); Mark Hatcher, Stamford, CT (US); Jiping Liu, Stamford, CT (US); Uchenna H. Iloeje, Stamford, CT (US); Abraham J. Langseth, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 0 days.

(21) Appl. No.: 18/608,735

(22) Filed: Mar. 18, 2024

Related U.S. Application Data

(63) Continuation of application No. PCT/US2024/020241, filed on Mar. 15, 2024.

(60) Provisional application No. 63/490,626, filed on Mar. 16, 2023.

(51) Int. Cl.
*A61K 31/166* (2006.01)
*A61K 9/00* (2006.01)
*A61K 9/48* (2006.01)

(52) U.S. Cl.
CPC .......... *A61K 31/166* (2013.01); *A61K 9/0053* (2013.01); *A61K 9/4825* (2013.01); *A61K 9/4833* (2013.01); *A61K 9/4858* (2013.01); *A61K 9/4866* (2013.01)

(58) Field of Classification Search
CPC .................................................. A61K 31/166
USPC ......................................................... 514/619
See application file for complete search history.

(56) References Cited

U.S. PATENT DOCUMENTS

| | | |
|---|---|---|
| 6,960,614 B2 | 11/2005 | Barrett et al. |
| 7,060,856 B2 | 6/2006 | Macikenas et al. |
| 11,066,358 B1 | 7/2021 | Irdam |
| 11,084,780 B1 | 8/2021 | Patterson et al. |
| 11,427,534 B1 | 8/2022 | Patterson et al. |
| 11,453,641 B2 | 9/2022 | Irdam |
| 11,571,402 B2 | 2/2023 | Patterson et al. |
| 11,806,321 B2 | 11/2023 | Iloeje et al. |
| 2023/0202985 A1* | 6/2023 | Vanderhoydonck ........................ C07D 487/04 514/274 |

OTHER PUBLICATIONS

"NF Consortium Protocol, NF Protocol 106,", A Phase 2 Trial of the MEK Inhibitor PD-0325901 in Adolescents and Adults with NF1-Associated Morbid Plexiform Neurofibromas, 2018, 89 pages.
Weiss , et al., "J. Clin. Oncol., 39(7):797-806, 2021".

* cited by examiner

*Primary Examiner* — Raymond J Henley, III
(74) *Attorney, Agent, or Firm* — Blank Rome LLP

(57) ABSTRACT

The present disclosure relates to an oral dosage form, such as a capsule, comprising (a) mirdametinib having a d90 no more than 250 microns, a d50 no more than 50 microns, or both, and (b) one or more pharmaceutically acceptable excipients. These dosage forms are useful in the treatment of tumors and cancers, such as plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain. The disclosure also related to improved dosage regimens for mirdametinib treatments.

30 Claims, 2 Drawing Sheets

DOSAGE FORMS OF MIRDAMETINIB

This application is a continuation of International Patent Application No. PCT/US2024/020241, filed Mar. 15, 2024, which claims the benefit of U.S. Provisional Application No. 63/490,626, filed Mar. 16, 2023, each of which is hereby incorporated by reference in its entirety

FIELD OF THE INVENTION

The present disclosure relates to an oral dosage form, such as a capsule, comprising (a) mirdametinib having a d90 no more than 250 microns, a d50 no more than 50 microns, or both, and (b) one or more pharmaceutically acceptable excipients. The disclosure also related to improved dosage regimens for mirdametinib treatments.

BACKGROUND

Mirdametinib is an allosteric, small molecule targeting mitogen-activated protein kinase kinase (MEK).

There is a need for effective treatments for treating neurofibromatosis type 1 (NF1) associated inoperable plexiform neurofibromas (PN).

BRIEF SUMMARY OF THE INVENTION

One aspect of the present invention is an oral dosage form comprising (a) mirdametinib having a d90 no more than 250 microns and (b) one or more pharmaceutically acceptable excipients. In one embodiment, the mirdametinib has a d90 ranging from 50 to 150 microns. In another embodiment, the mirdametinib has a d90 ranging from 150 to 250 microns. In yet another embodiment, the mirdametinib has a d50 of no more than 50 microns. In yet another embodiment, the mirdametinib has a d50 of 1 to 25 microns. In yet another embodiment, the mirdametinib has a d50 of 25 to 50 microns. In yet another embodiment, the mirdametinib has a d50 of no more than 30 microns. The oral dosage form may be a solid oral dosage form, such as a capsule or tablet (e.g., dispersible tablet). In one embodiment, the oral dosage form contains 1 mg mirdametinib. In another embodiment, the oral dosage form contains 2 mg mirdametinib.

Another aspect is an oral dosage form comprising (a) mirdametinib having a d50 no more than 50 microns and (b) one or more pharmaceutically acceptable excipients. In one embodiment, the mirdametinib has a d50 of 1 to 25 microns. In yet another embodiment, the mirdametinib has a d50 of 25 to 50 microns. In yet another embodiment, the mirdametinib has a d50 of no more than 30 microns. The oral dosage form may be a solid oral dosage form, such as a capsule or tablet (e.g., dispersible tablet). In one embodiment, the oral dosage form contains 1 mg mirdametinib. In another embodiment, the oral dosage form contains 2 mg mirdametinib.

In one embodiment, the dosage form is a capsule prepared by (i) roller compaction of a blend of the mirdametinib and one or more pharmaceutically acceptable excipients and (ii) encapsulating the compacted blend into a capsule.

Another aspect is an oral dosage form comprising (a) 1 mg mirdametinib having a d90 no more than 250 microns and (b) one or more pharmaceutically acceptable excipients, wherein the dosage form provides upon oral administration, on the first day of treatment with mirdametinib, an $AUC_{0-12h}$ less than 400 ng·h/mL, a $C_{max}$ no more than 40 ng/ml, or both. In one embodiment, the dosage form provides upon oral administration, on the first day of treatment with mirdametinib, an $AUC_{0-12h}$ less than 200 ng·h/mL. In another embodiment, the dosage form provides upon oral administration, on the first day of treatment with mirdametinib, $AUC_{0-12h}$ less than 100 ng·h/mL. In yet another embodiment, the dosage form provides upon oral administration, on the first day of treatment with mirdametinib, a $C_{max}$ no more than 32 ng/mL. In yet another embodiment, the dosage form provides upon oral administration, on the first day of treatment with mirdametinib, a $C_{max}$ no more than 30 ng/mL.

Yet another aspect is an oral dosage form comprising (a) 1 mg mirdametinib having a d50 no more than 50 microns and (b) one or more pharmaceutically acceptable excipients, wherein the dosage form provides upon oral administration, on the first day of treatment with mirdametinib, an $AUC_{0-12h}$ less than 400 ng·h/mL, a $C_{max}$ no more than 40 ng/mL, or both. In one embodiment, the dosage form provides upon oral administration, on the first day of treatment with mirdametinib, an $AUC_{0-12h}$ less than 200 ng·h/mL. In another embodiment, the dosage form provides upon oral administration, on the first day of treatment with mirdametinib, $AUC_{0-12h}$ less than 100 ng·h/mL. In yet another embodiment, the dosage form provides upon oral administration, on the first day of treatment with mirdametinib, a $C_{max}$ no more than 32 ng/ml. In yet another embodiment, the dosage form provides upon oral administration, on the first day of treatment with mirdametinib, a $C_{max}$ no more than 30 ng/mL.

In one embodiment, the oral dosage form of any embodiment described herein releases at least 80% of its mirdametinib within 15 minutes as measured according to the USP basket method in 0.1 N HCl (0.1 N HCL aqueous solution) and at 75 rpm.

Yet another aspect is a method of treating a human patient (e.g., 2 years or older) who has neurofibromatosis type 1 (NF1) associated inoperable plexiform neurofibromas (PN) comprising orally administering an effective amount of one or more oral dosage forms described herein to the patient. In one embodiment, the patient has symptomatic, inoperable plexiform neurofibromas.

Yet another aspect is a method of treating a human patient who has neurofibromatosis type 1 (NF1) associated inoperable plexiform neurofibromas (PN) that is progressing or causing significant morbidity comprising orally administering an effective amount of one or more oral dosage forms described herein to the patient.

In one embodiment of any of the methods described herein, the patient has progressive PN (i.e., a 20% increase in PN volume documented by comparison of two MRI scans in the time period of 12 months or less prior to the first dose of mirdametinib).

In one embodiment of any of the methods described herein, the patient has PNs that cause significant morbidity.

In one embodiment of any of the methods described herein, the patient has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function, or painful lesions. In one embodiment, the lesions causing major deformity or are significantly disfiguring are tumors of the head and neck or those on other areas of the body that are unable to be concealed by standard garments.

In one embodiment of any of the methods described herein, the patient has paraspinal lesions.

In one embodiment of any of the methods described herein, the patient has a Lansky performance of at least 60%.

In one embodiment of any of the methods described herein, the patient has the clinical diagnosis of NF1 using the NIH Consensus Conference and one or more of the following:
- (a) six or more café-au-lait macules with a diameter >5 mm in prepubertal and >15 mm in post-pubertal individuals;
- (b) freckling in axilla or inguinal regions;
- (c) optic glioma;
- (d) two or more Lisch nodules;
- (e) a distinctive bony lesion (dysplasia of the sphenoid bone or dysplasia of thinning of long bone cortex); and
- (f) a first degree relative with NF1.

In one embodiment of any of the methods described herein, the patient has a constitutional NF1 mutation documented in a Clinical Laboratory Improvement Amendments/College of American Pathologists certified lab.

In one embodiment of any of the methods described herein, the patient either (a) has a parent diagnosed with NF1 and one or more criteria of (1) through (7), or (b) does not have a parent diagnosed with NF1 but has two or more criteria of (1) through (7):
- (1) six or more café-au-lait macules over 5 mm in greatest diameter in prepubertal individuals and over 15 mm in greatest diameter in post-pubertal individuals;
- (2) freckling in the axillary or inguinal region;
- (3) two or more neurofibromas of any type or one plexiform neurofibroma;
- (4) optic pathway glioma;
- (5) two or more iris Lisch nodules identified by slit lamp examination or two or more choroidal abnormalities (defined as bright, patchy nodules imaged by optical coherence tomography (OCT)/near-infrared reflectance (NIR) imaging;
- (6) a distinctive osseus lesion (such as sphenoid dysplasia, anterolateral bowing of the tibia, or pseudarthrosis of a long bone); and
- (7) a heterozygous pathogenic NF1 variant with a variant allele fraction of 50% in apparently normal tissue such as white blood cells.

In one embodiment of any of the methods described herein, the patient is 2 to 15 years of age. In another embodiment of any of the methods described herein, the patient is at least 16 years of age.

In one embodiment, about 2 mg/m$^2$ mirdametinib is administered to the patient twice daily.

In another embodiment of any of the methods described herein,
- (a) for a patient having a body surface area no more than 0.69 m$^2$, the patient is initially orally administered 1 mg mirdametinib twice daily (i.e., a total of 2 mg daily),
- (b) for a patient having a body surface area of 0.7 to 1.04 m$^2$, the patient is initially orally administered 2 mg mirdametinib twice daily (i.e., a total of 4 mg daily),
- (c) for a patient having a body surface area of 1.05 to 1.49 m$^2$, the patient is initially orally administered 3 mg mirdametinib twice daily (i.e., a total of 6 mg daily), and
- (d) for a patient having a body surface area of at least 1.5 m$^2$, the patient is initially orally administered 4 mg mirdametinib twice daily (i.e., a total of 8 mg daily).

In yet another embodiment of any of the methods described herein,
- (a) for a patient having a body surface area of up to 0.59 m$^2$ or 0.4 to 0.59 m$^2$, the patient is initially orally administered 1 mg mirdametinib twice daily,
- (b) for a patient having a body surface area of 0.6 to 0.79 m$^2$, the patient is initially orally administered 1.5 mg mirdametinib twice daily,
- (c) for a patient having a body surface area of 0.8 to 0.99 m$^2$, the patient is initially orally administered 2 mg mirdametinib twice daily,
- (d) for a patient having a body surface area of 1.0 to 1.19 m$^2$, the patient is initially orally administered 2.5 mg mirdametinib twice daily,
- (e) for a patient having a body surface area of 1.2 to 1.39 m$^2$, the patient is initially orally administered 3 mg mirdametinib twice daily,
- (f) for a patient having a body surface area of 1.4 to 1.59 m$^2$, the patient is initially orally administered 3.5 mg mirdametinib twice daily, and
- (g) for a patient having a body surface area of at least 1.6 m$^2$, the patient is initially orally administered 4 mg mirdametinib twice daily. In one embodiment, the patient is less than 12 years of age. In one embodiment, the mirdametinib is administered in the form of one or more tablets (such as one or more dispersible tablets). In another embodiment, the mirdametinib is administered in the form of one or more 0.5 mg tablets, one or more 1 mg tablets, or any combination of any of the foregoing. The tablets may be dispersible tablets. One embodiment is a method of treating a human patient who has neurofibromatosis type 1 (NF1) associated inoperable plexiform neurofibromas (PN) (or any such patient as described herein) comprising the method of administration of mirdametinib described above.

In yet another embodiment of any of the methods described herein,
- (a) for a patient having a body surface area of up to 0.69 m$^2$ or 0.4 to 0.69 m$^2$, the patient is initially orally administered 1 mg mirdametinib twice daily,
- (b) for a patient having a body surface area of 0.7 to 1.04 m$^2$, the patient is initially orally administered 2 mg mirdametinib twice daily,
- (c) for a patient having a body surface area of 1.05 to 1.49 m$^2$, the patient is initially orally administered 3 mg mirdametinib twice daily, and
- (d) for a patient having a body surface area of at least 1.5 m$^2$, the patient is initially orally administered 4 mg mirdametinib twice daily. In one embodiment, the patient is at least 12 years of age. In one embodiment, the mirdametinib is administered in the form of one or more capsules, such as in the form of one or more 1 mg capsules, one or more 2 mg capsules, or any combination of any of the foregoing. One embodiment is a method of treating a human patient who has neurofibromatosis type 1 (NF1) associated inoperable plexiform neurofibromas (PN) (or any such patient as described herein) comprising the method of administration of mirdametinib described above.

In yet another embodiment of any of the methods described herein,
- (a) for a patient having a body surface area of 0.4 to 0.59 m$^2$ (or up to 0.59 m$^2$), the patient is initially orally administered 1 mg mirdametinib twice daily,
- (b) for a patient having a body surface area of 0.6 to 0.79 m$^2$, the patient is initially orally administered 1.5 mg mirdametinib twice daily,
- (c) for a patient having a body surface area of 0.8 to 0.99 m$^2$, the patient is initially orally administered 2 mg mirdametinib twice daily, (d) for a patient having a body surface area of 1.0 to 1.39 m², the patient is initially orally administered 2.5 mg mirdametinib twice daily, (e) for a patient having a body surface area of 1.4 to 1.59 m², the patient is initially orally administered 3 mg mirdametinib twice daily, (f) for a patient having a body surface area of 1.6 to 1.69 m², the patient is initially orally administered 3.5 mg mirdametinib twice daily, and (g) for a patient having a body surface area of at least 1.7 m², the patient is initially orally administered 4 mg mirdametinib twice daily. In one embodiment, the patient is less than 12 years of age. In one embodiment, the mirdametinib is administered in the form of one or more tablets (such as one or more dispersible tablets). In another embodiment, the mirdametinib is administered in the form of one or more 0.5 mg tablets, one or more 1 mg tablets, or any combination of any of the foregoing. The tablets may be dispersible tablets. One embodiment is a method of treating a human patient who has neurofibromatosis type 1 (NF1) associated inoperable plexiform neurofibromas (PN) (or any such patient as described herein) comprising the method of administration of mirdametinib described above.

One embodiment is a method of administering mirdametinib to a patient (such as a human patient) in need thereof by orally administering mirdametinib to the patient, where (a) for a patient having a body surface area of 0.4 to 0.59 m² (or up to 0.59 m²), the patient is initially orally administered 1 mg mirdametinib twice daily, (b) for a patient having a body surface area of 0.6 to 0.79 m², the patient is initially orally administered 1.5 mg mirdametinib twice daily, (c) for a patient having a body surface area of 0.8 to 0.99 m², the patient is initially orally administered 2 mg mirdametinib twice daily, (d) for a patient having a body surface area of 1.0 to 1.19 m², the patient is initially orally administered 2.5 mg mirdametinib twice daily, (e) for a patient having a body surface area of 1.2 to 1.39 m², the patient is initially orally administered 3 mg mirdametinib twice daily, (f) for a patient having a body surface area of 1.4 to 1.59 m², the patient is initially orally administered 3.5 mg mirdametinib twice daily, and (g) for a patient having a body surface area of at least 1.6 m², the patient is initially orally administered 4 mg mirdametinib twice daily. In one embodiment, the patient is less than 12 years of age. In one embodiment, the mirdametinib is administered in the form of one or more tablets (such as one or more dispersible tablets). In another embodiment, the mirdametinib is administered in the form of one or more 0.5 mg tablets, one or more 1 mg tablets, or any combination of any of the foregoing. The tablets may be dispersible tablets. In one embodiment, the mirdametinib may have the d50, d90, or both as described herein. In another embodiment, the mirdametinib is administered as a dosage form, such as a tablet (e.g., dispersible tablet) or capsule, as described herein. One embodiment is a method of treating a human patient who has neurofibromatosis type 1 (NF1) associated inoperable plexiform neurofibromas (PN) (or any such patient as described herein) comprising the method of administration of mirdametinib described above.

Another embodiment is a method of administering mirdametinib to a patient (such as a human patient) in need thereof by orally administering mirdametinib to the patient, where (a) for a patient having a body surface area of 0.4 to 0.69 m² (or up to 0.69 m²), the patient is initially orally administered 1 mg mirdametinib twice daily, (b) for a patient having a body surface area of 0.7 to 1.04 m², the patient is initially orally administered 2 mg mirdametinib twice daily, (c) for a patient having a body surface area of 1.05 to 1.49 m², the patient is initially orally administered 3 mg mirdametinib twice daily, and (d) for a patient having a body surface area of at least 1.5 m², the patient is initially orally administered 4 mg mirdametinib twice daily. In one embodiment, the patient is at least 12 years of age. In one embodiment, the mirdametinib is administered in the form of one or more capsules, such as in the form of one or more 1 mg capsules, one or more 2 mg capsules, or any combination of any of the foregoing. One embodiment is a method of treating a human patient who has neurofibromatosis type 1 (NF1) associated inoperable plexiform neurofibromas (PN) (or any such patient as described herein) comprising the method of administration of mirdametinib described above.

Yet another embodiment is a method of administering mirdametinib to a patient (such as a human patient) in need thereof by orally administering mirdametinib to the patient, where (a) for a patient having a body surface area of 0.4 to 0.59 m² (or up to 0.59 m²), the patient is initially orally administered 1 mg mirdametinib twice daily, (b) for a patient having a body surface area of 0.6 to 0.79 m², the patient is initially orally administered 1.5 mg mirdametinib twice daily, (c) for a patient having a body surface area of 0.8 to 0.99 m², the patient is initially orally administered 2 mg mirdametinib twice daily, (d) for a patient having a body surface area of 1.0 to 1.39 m², the patient is initially orally administered 2.5 mg mirdametinib twice daily, (e) for a patient having a body surface area of 1.4 to 1.59 m², the patient is initially orally administered 3 mg mirdametinib twice daily, (f) for a patient having a body surface area of 1.6 to 1.69 m², the patient is initially orally administered 3.5 mg mirdametinib twice daily, and (g) for a patient having a body surface area of at least 1.7 m², the patient is initially orally administered 4 mg mirdametinib twice daily. In one embodiment, the patient is less than 12 years of age. In one embodiment, the mirdametinib is administered in the form of one or more tablets (such as one or more dispersible tablets). In another embodiment, the mirdametinib is administered in the form of one or more 0.5 mg tablets, one or more 1 mg tablets, or any combination of any of the foregoing. The tablets may be dispersible tablets. One embodiment is a method of treating a human patient who has neurofibromatosis type 1 (NF1) associated inoperable plexiform neurofibromas (PN) (or any such patient as described herein) comprising the method of administration of mirdametinib described above.

In one embodiment of any of the methods described herein, the maximum daily dose is 4 mg mirdametinib twice daily.

In one embodiment of any of the methods described herein, over each four week period, the mirdametinib is administered for the first three weeks and discontinued for the last one week.

In any of the methods described herein, where the dosage form is a tablet (such as a dispersible tablet), the tablet or tablets to be administered may first be dispersed in water (such as drinking water) (for instance, about 5 to 10 mL of water) to form an oral suspension, optionally swirled so that no lumps remain, and administered (preferably within 30 minutes). In some embodiments, the one or more oral tablets are dispersed in about 5 to about 10 mL of water in a container, wherein the tablets are swirled so no lumps remain in the water. In some embodiments, the oral suspension is to be administered within 30 minutes. In some instances, the patient rinses the container with the suspension with additional drinking water (for instance, about 5 to 10 mL of water) and administer to the patient to ensure the full dose is taken.

In one embodiment of any of the methods described herein, the dose administered is reduced due to an adverse event, wherein the dose is reduced as follows:
(a) if the dose at the time of the event is 1 mg mirdametinib twice daily, then the reduced daily dose is 1 mg administered in the morning only;
(b) if the dose at the time of the event is 2 mg mirdametinib twice daily, then the reduced daily dose is 2 mg administered in the morning and 1 mg administered in the afternoon or evening;
(c) if the dose at the time of the event is 3 mg mirdametinib twice daily, then the reduced daily dose is 2 mg administered twice daily; and
(d) if the dose at the time of the event is 4 mg mirdametinib twice daily, then the reduced daily dose is 3 mg administered twice daily. In one embodiment of any of the methods described herein, the adverse event resulting in the dose reduction is acneiform.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis. In one embodiment, in step (i), mirdametinib is selected based on a response rate of at least 70%. In another embodiment, in step (i), mirdametinib is selected based on a response rate of at least 75%. In yet another embodiment, in step (i), mirdametinib is selected based on a response rate of at least 80%. In yet another embodiment, in step (i), mirdametinib is selected based on a response rate of at least 85%. In yet another embodiment, in step (i), mirdametinib is selected based on a response rate of at least 90%. In yet another embodiment, in step (i), mirdametinib is selected based on a response rate of at least 95%.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the treatment results in decreased pain intensity.

In one embodiment of any of the methods described herein, the treatment results in decreased pain interference.

Another aspect is a method for treating a tumor or cancer in a human patient selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain, comprising administering to the patient one or more oral dosage forms comprising mirdametinib as described herein.

In some aspects, a therapeutically effective amount of mirdametinib, or a pharmaceutically acceptable salt thereof, is orally administered. In some aspects, the mirdametinib, or a pharmaceutically acceptable salt thereof, is orally administered in an amount of about 1 mg/m$^2$ to about 10 mg/m$^2$ per day based on mirdametinib free base. In some aspects, the mirdametinib, or a pharmaceutically acceptable salt thereof, is orally administered in an amount of about 1 mg to about 10 mg per day based on mirdametinib free base.

In some aspects, the mirdametinib, or a pharmaceutically acceptable salt thereof, is orally administered in a single dosage form comprising about 0.1 mg/m$^2$ to about 10 mg/m$^2$ based on mirdametinib free base. In some aspects, the mirdametinib, or a pharmaceutically acceptable salt thereof, is administered in a single dosage form comprising about 0.1 mg to about 10 mg based on mirdametinib free base.

In some aspects, the mirdametinib, or a pharmaceutically acceptable salt thereof, is administered once daily. In some aspects, the mirdametinib, or a pharmaceutically acceptable salt thereof, is administered twice daily.

In some aspects, the mirdametinib, or a pharmaceutically acceptable salt thereof, exhibits high blood-brain-barrier penetration.

In some aspects, the patient is a human. In some aspects, the human has an age of ≥2 and <25.

In some aspects, the human has had no prior exposure to MEK inhibitors.

In some aspects, the mirdametinib, or a pharmaceutically acceptable salt thereof, is administered as a monotherapy to treat the tumor or cancer. In some aspects, the mirdametinib, or a pharmaceutically acceptable salt thereof, is administered in combination with another active ingredient and/or surgery to treat the tumor or cancer.

In any of the embodiments herein, the dose of mirdametinib may be administered with one or more 0.5 mg, 1 mg or 2 mg mirdametinib dosage forms or any combination of any of the foregoing. For example, a 3.5 mg dose can be administered as three 1 mg mirdametinib dosage forms (e.g., tablets) and one 0.5 mg mirdametinib dosage form (e.g., tablet).

In one embodiment, mirdametinib is provided as 0.5 or 1 mg mirdametinib tablets (e.g., dispersible tablets). In another embodiment, mirdametinib is provided as 1 or 2 mg mirdametinib capsules. In yet another embodiment, mirdametinib is provided as 0.5 or 1 mg mirdametinib tablets (e.g., dispersible tablets) and 1 or 2 mg mirdametinib capsules.

DETAILED DESCRIPTION OF THE INVENTION

I. Definitions

Figure 1:
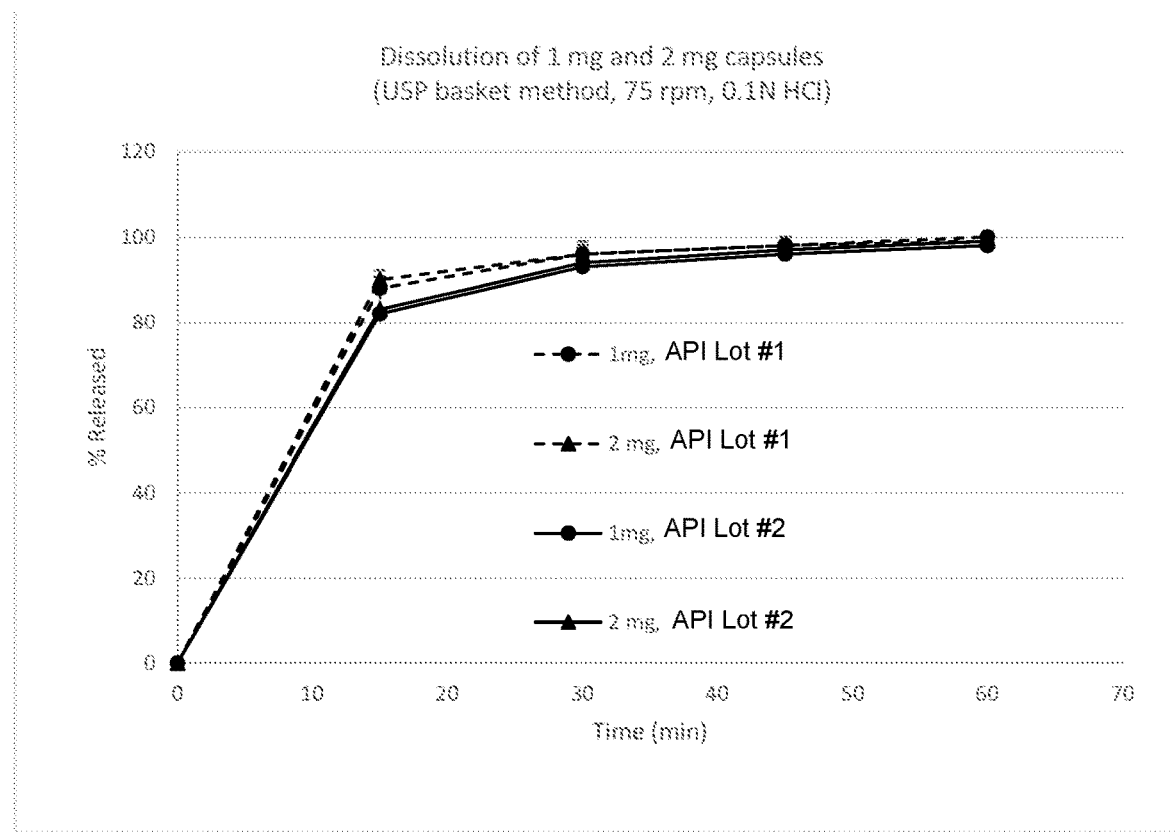
FIG. 1 is a graph showing the release of mirdametinib according to the USP basket method in 0.1 N HCl and at 75 rpm from 1 mg and 2 mg capsules prepared with mirdametinib from Lots #1 and #2 as described in Example 2.

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "mirdametinib" refers to the single enantiomer N—((R)-2,3-dihydroxypropoxy)-3,4-difluoro-2-(2-fluoro-4-iodo-phenylamino)benzamide. The teachings throughout the specification regarding mirdametinib equally apply to pharmaceutically acceptable salts of mirdametinib. For instance, the disclosure of a method of treating neurofibromatosis type 1 (NF1) associated inoperable plexiform neurofibromas (PN) with mirdametinib also means that a pharmaceutically acceptable salt of mirdametinib can be administered to treat NF1 associated inoperable PN.

The term "mg/m$^2$" refers to the dose in milligrams per m$^2$ body surface area of the patient.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "$AUC_{0-12h}$" refers to the area under the plasma concentration-time curve from time 0 to the end of 12 hours.

The term "$C_{max}$" refers to the maximum plasma concentration.

The term "dispersible" as used herein refers to a composition (e.g., a tablet, powder, granules, minitablets, or pellets) which disintegrates and/or dissolves when combined with water or another potable liquid (e.g., a non-water beverage), or a subject's own saliva when placed in the subject's mouth, with or without the addition of agitation or temperature modification. In some aspects, the dispersible composition disintegrates or dissolves within 10 minutes, 9 minutes, 8 minutes, 7 minutes, 6 minutes, 5 minutes, 4 minutes, 3 minutes, 2 minutes, or 1 minute after being combined with water or another potable liquid. Such disintegration or dissolution need not be complete. For example, a dispersible tablet may dissolve almost entirely, but some undissolved particulate matter may remain.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy*, 21st Edition, Lippincott Williams & Wilkins: Philadelphia, PA, 2005; *Handbook of Pharma-* ceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, Gibson Ed., CRC Press LLC: Boca Raton, F L, 2004 (incorporated herein by reference).

The term "pharmaceutically acceptable salts" refers to the relatively non-toxic, inorganic and organic acid addition salts of mirdametinib. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts. See, e.g., Berge et al. (1977) "Pharmaceutical Salts", J. Pharm. Sci. 66:1-19.

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, "D50" or "d50", also known as the median diameter, corresponds to the value under which 50% of the particles has a lower volume diameter. "D90" or "d90" corresponds to the value under which 90% of the particles has a lower volume diameter. The particle size may be measured using wet standard laser diffraction particle sizing techniques known in the art. One example of an instrument to measure the particle size of the dry powders is the Mastersizer 3000, manufactured by Malvern Panalytical Ltd. (Malvern, UK). As particles are often non-spherical, it is difficult and complex to provide dimensional descriptions of these non-spherical particles. As used herein, "volume diameter" refers to diameter of a sphere with equal volume of the non-spherical particle.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Oral Dosage Forms

The oral dosage form contains mirdametinib having a d90 no more than 250 microns, d50 no more than 50 microns, or both. In one embodiment, the oral dosage form contains 0.5 mg mirdametinib, 1.0 mirdametinib, 1.5 mg mirdametinib, 2.0 mg mirdametinib, 2.5 mg mirdametinib, 3.0 mg mirdametinib, 3.5 mg mirdametinib, or 4.0 mg mirdametinib.

In one embodiment, the oral dosage form contains 0.5 mg mirdametinib.

In another embodiment, the oral dosage form contains 1.0 mg mirdametinib.

In another embodiment, the oral dosage form contains 2.0 mg mirdametinib.

The mirdametinib may be present in a crystalline form in the oral dosage form, such as any of those described in U.S. Pat. Nos. 6,960,614, 7,060,856, 11,066,358, and 11,084,780, which are hereby incorporated by reference in their entireties. In some aspects, the crystalline form of mirdametinib is selected from (a) a crystalline form (Form IV) of mirdametinib characterized by an X-ray powder diffraction (XRPD) pattern having peaks at 4.6±0.2, 7.3±0.2, and 14.6±0.2 degrees two theta; (b) a crystalline form (Form I) of mirdametinib characterized by an XRPD pattern having peaks at 10.6±0.2, 13.7±0.2, 19.0±0.2, and 23.7±0.2 degrees two theta; and (c) a crystalline form (Form II) of mirdametinib characterized by an XRPD pattern having peaks at 5.5±0.2 and 19.6±0.2 degrees two theta.

In some aspects, the crystalline form (Form IV) of mirdametinib is characterized by an XRPD pattern having peaks at 4.6±0.2, 7.3±0.2 (or 7.2±0.2), and 14.6±0.2 degrees two theta (Form IV). In some aspects, the crystalline form of mirdametinib is characterized by an XRPD pattern having peaks at 4.6±0.2, 7.3±0.2 (or 7.2±0.2), 14.6±0.2, and 25.0±0.2 degrees two theta.

In some aspects, the crystalline form of mirdametinib is characterized by a differential scanning calorimetry (DSC) profile which does not include an endotherm with an onset at about 117° C.

In some aspects, the crystalline form of mirdametinib does not contain any amount of Form I or Form II detectable by XRPD and/or DSC. Forms I and II are described in U.S. Pat. No. 6,960,614.

In some aspects, the crystalline form mirdametinib is anhydrous.

In some aspects, the crystalline form mirdametinib is Form IV. In some aspects, the crystalline form of mirdametinib is essentially pure Form IV (such as described in U.S. Pat. No. 11,066,358, which is hereby incorporated by reference). Form IV is described in described in U.S. Pat. Nos. 7,060,856 and 11,066,358. In some aspects, the essentially pure Form IV of mirdametinib exhibits an XRPD pattern and/or DSC profile which is substantially unchanged after storage for 3 months at standard warehouse conditions (15° C.-25° C. and ≤65% relative humidity). In some aspects, the essentially pure Form IV of mirdametinib exhibits an XRPD pattern and/or DSC profile which is substantially unchanged after storage for 6 months at standard warehouse conditions (15° C.-25° C. and ≤65% relative humidity). In some aspects, the essentially pure Form IV of mirdametinib exhibits an XRPD pattern and/or DSC profile which is substantially unchanged after storage for 1 year at standard warehouse conditions (15° C.-25° C. and ≤65% relative humidity).

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Göebel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers. In some aspects, the DSC pattern is generated using a TA Instruments Q100 or Q2000 differential scanning calorimeter at a rate of temperature increase of about 15° C./min.

The oral dosage form may contain one or more diluents, disintegrants, lubricants, or any combination of any of the foregoing. In one embodiment, the oral dosage form comprises (a) about 0.1 w/w % to about 5 w/w % wt/wt % of mirdametinib, (b) about 50 w/w % to about 98 w/w % of one or more diluents; (c) about 1 w/w % to about 10 w/w % of one or more disintegrants; and (d) up to about 5 w/w % of one or more lubricants.

Suitable diluents include, but are not limited to, microcrystalline cellulose, lactose, mannitol, sorbitol, xylitol, sucrose, starch, pregelatinized starch, calcium sulfate, calcium carbonate, dibasic calcium phosphate, and any combination of any of the foregoing. In one embodiment, the oral dosage form includes the diluent microcrystalline cellulose.

Suitable disintegrants include, but are not limited to, croscarmellose sodium, sodium starch glycolate, crospovidone, microcrystalline cellulose, starch, pregelatinized starch, low substituted hydroxypropyl cellulose, alginic acid, and any combination of any of the foregoing. In one embodiment, the oral dosage form includes the disintegrant croscarmellose sodium.

Suitable lubricants include, but are not limited to, magnesium stearate, stearic acid, calcium stearate, zinc stearate, beeswax, colloidal silicon dioxide, hydrogenated vegetable oil, sodium stearyl fumarate, glycerol dibehenate, talc, and any combination of any of the foregoing. In one embodiment, the oral dosage form includes the lubricant magnesium stearate.

The oral dosage form can be a capsule, such as a hard gelatin capsule.

The oral dosage form can comprise one or more pharmaceutically acceptable carriers. In some aspects, the oral dosage form is dispersible. In some aspects, the oral dosage form is orodispersible. The oral dosage form may be a tablet, a powder, granules, minitablets, or pellets (also called beads). In some aspects, the oral dosage form is a powder. In some aspects, the oral dosage form is a dispersible powder. In some aspects, a capsule or sachet comprises the dispersible powder. In some aspects, the oral dosage form is in the form of granules. In some aspects, the granules are dispersible granules. In some aspects, a capsule or sachet comprises the dispersible granules. In some aspects, the oral dosage form is in the form of minitablets. In some aspects, the minitablets are dispersible minitablets. In some aspects, a capsule or sachet comprises the dispersible minitablets. In some aspects, the oral dosage form is in the form of pellets. In some aspects, the pellets are dispersible pellets. In some aspects, a capsule or sachet comprises the dispersible pellets.

In some aspects, the oral dosage form is a tablet. In some aspects, the tablet is a dispersible tablet. In some aspects, the tablet is an orodispersible tablet.

In some aspects, the oral dosage form that is a dispersible tablet, dispersible powder, dispersible granules, dispersible minitablets, or dispersible pellets comprises about 0.1 mg to about 20 mg of mirdametinib, wherein each component of the oral dosage form is as follows: (a) about 0.1 wt/wt % to about 7 wt/wt % of mirdametinib; (b) about 50 wt/wt % to about 98 wt/wt % of one or more diluents; (c) about 1 wt/wt % to about 10 wt/wt % of one or more disintegrants; (d) optionally 0 wt/wt % to about 5 wt/wt % of one or more flavoring agents; (e) optionally 0 wt/wt % to about 5 wt/wt % of one or more sweeteners; and (f) optionally 0 wt/wt % to about 5 wt/wt % of one or more lubricants.

In some aspects, the oral dosage form that is a dispersible tablet, dispersible powder, dispersible granules, dispersible minitablets, or dispersible pellets comprises about 0.1 mg to about 20 mg of mirdametinib, wherein each component of the oral dosage form is as follows: (a) about 0.2 wt/wt % to about 1.5 wt/wt % of mirdametinib; (b) about 75 wt/wt % to about 98 wt/wt % of one or more diluents; (c) about 3 wt/wt % to about 8 wt/wt % of one or more disintegrants; (d) optionally 0 wt/wt % to about 5 wt/wt % of one or more flavoring agents; (e) optionally 0 wt/wt % to about 5 wt/wt % of one or more sweeteners; and (f) optionally 0 wt/wt % to about 5 wt/wt % of one or more lubricants.

In some aspects, the oral dosage form that is a dispersible tablet, dispersible powder, dispersible granules, dispersible minitablets, or dispersible pellets comprises about 0.1 mg to about 20 mg of mirdametinib, wherein each component of the oral dosage form is as follows: (a) about 0.5 wt/wt % to about 1.2 wt/wt % of mirdametinib; (b) about 85 wt/wt % to about 95 wt/wt % of one or more diluents; (c) about 3.5 wt/wt % to about 6 wt/wt % of one or more disintegrants; (d) optionally 0 wt/wt % to about 2.5 wt/wt % of one or more flavoring agents; (e) optionally 0 wt/wt % to about 2 wt/wt % of one or more sweeteners; and (f) optionally about 0.5 wt/wt % to about 2 wt/wt % of one or more lubricants.

In some aspects, the oral dosage form that is a dispersible tablet, dispersible powder, dispersible granules, dispersible minitablets, or dispersible pellets comprises about 0.5 mg of mirdametinib. In some aspects, the oral dosage form comprises about 1 mg of mirdametinib. In some aspects, the oral dosage form that is a dispersible tablet, dispersible powder, dispersible granules, dispersible minitablets, or dispersible pellets comprises about 2 mg of mirdametinib. In some aspects, the oral dosage form that is a dispersible tablet, dispersible powder, dispersible granules, dispersible minitablets, or dispersible pellets comprises about 3 mg of mirdametinib. In some aspects, the oral dosage form that is a dispersible tablet, dispersible powder, dispersible granules, dispersible minitablets, or dispersible pellets comprises about 4 mg of mirdametinib.

In some aspects, at least one of the diluents is selected from microcrystalline cellulose, lactose, mannitol, sorbitol, xylitol, sucrose, starch, pregelatinized starch, calcium sulfate, calcium carbonate and dibasic calcium phosphate. In some aspects, at least one of the diluents is microcrystalline cellulose.

In some aspects, at least one of the disintegrants is selected from croscarmellose sodium, sodium starch glycolate, crospovidone, microcrystalline cellulose, starch, pregelatinized starch, low substituted hydroxypropyl cellulose, and alginic acid. In some aspects, at least one of the disintegrants is croscarmellose sodium.

In some aspects, at least one of the flavoring agents is selected from natural or synthetic flavors including but not limited to, grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring. In some aspects, at least one of the flavoring agents is grape flavoring.

In some aspects, at least one of the sweeteners is selected from sucralose, acesulfame, saccharin, sucrose, xylitol, mannitol, sorbitol, glucose, fructose, and aspartame. In some aspects, at least one of the sweeteners is sucralose.

In some aspects, at least one of the lubricants is selected from magnesium stearate, stearic acid, calcium stearate, zinc stearate, beeswax, colloidal silicon dioxide, hydrogenated vegetable oil, sodium stearyl fumarate, glycerol dibehenate, and talc. In some aspects, at least one of the lubricants is magnesium stearate.

III. Methods of Treatment

Methods for treating a tumor or cancer selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain, comprising administering to a patient in need thereof mirdametinib or a pharmaceutically acceptable salt thereof are provided herein.

In some aspects of any of the methods described herein, the tumor or cancer is plexiform neurofibromas. In some aspects, the tumor or cancer is plexiform neurofibromas associated with neurofibromatosis type 1.

In some aspects of any of the methods described herein, the tumor or cancer is high grade glioma. In some aspects, the high grade glioma is a primary cancer. In some aspects, the high grade glioma is a metastatic cancer.

In some aspects of any of the methods described herein, the tumor or cancer is low grade ovarian cancer. In some aspects, the tumor or cancer is Langerhans cell histiocytosis. In some aspects, the tumor or cancer is brain cancer. In some aspects, the tumor or cancer is a cancer that has metastasized to the patient's brain including lung cancer, breast cancer and melanoma.

In some aspects of any of the methods described herein, a therapeutically effective amount of mirdametinib, or a pharmaceutically acceptable salt thereof, is orally administered.

In some aspects of any of the methods described herein, the mirdametinib, or a pharmaceutically acceptable salt thereof, is administered in an amount of about 1 mg/m$^2$ to about 10 mg/m$^2$ per day based on mirdametinib free base, about 1.5 mg/m$^2$ to about 9.5 mg/m$^2$ per day based on mirdametinib free base, about 2 mg/m$^2$ to about 9 mg/m$^2$ per day based on mirdametinib free base, about 2.5 mg/m$^2$ to about 8.5 mg/m$^2$ per day based on mirdametinib free base, about 3 mg/m$^2$ to about 8 mg/m$^2$ per day based on mirdametinib free base, about 3.5 mg/m$^2$ to about 7.5 mg/m$^2$ per day based on mirdametinib free base, about 4 mg/m$^2$ to about 7 mg/m$^2$ per day based on mirdametinib free base, about 4.5 mg/m$^2$ to about 6.5 mg/m$^2$ per day based on mirdametinib free base, or about 5 mg/m$^2$ to about 6 mg/m$^2$ per day based on mirdametinib free base. In some aspects, the mirdametinib, or a pharmaceutically acceptable salt thereof, is administered in an amount of about 1 mg/m$^2$ per day based on mirdametinib free base, about 1.5 mg/m$^2$ per day based on mirdametinib free base, about 2 mg/m$^2$ per day based on mirdametinib free base, about 2.5 mg/m$^2$ per day based on mirdametinib free base, about 3 mg/m$^2$ per day based on mirdametinib free base, about 3.5 mg/m$^2$ per day based on mirdametinib free base, about 4 mg/m$^2$ per day based on mirdametinib free base, about 4.5 mg/m$^2$ per day based on mirdametinib free base, about 5 mg/m$^2$ per day based on mirdametinib free base, about 5.5 mg/m$^2$ per day based on mirdametinib free base, about 6 mg/m$^2$ per day based on mirdametinib free base, about 6.5 mg/m$^2$ per day based on mirdametinib free base, about 7 mg/m$^2$ per day based on mirdametinib free base, about 7.5 mg/m$^2$ per day based on mirdametinib free base, about 8 mg/m$^2$ per day based on mirdametinib free base, about 8.5 mg/m$^2$ per day based on mirdametinib free base, about 9 mg/m$^2$ per day based on mirdametinib free base, about 9.5 mg/m$^2$ per day based on mirdametinib free base, or about 10 mg/m$^2$ per day based on mirdametinib free base.

In some aspects of any of the methods described herein, the mirdametinib, or a pharmaceutically acceptable salt thereof, is administered in an amount of about 1 mg to about 10 mg per day based on mirdametinib free base, about 1.5 mg to about 9.5 mg per day based on mirdametinib free base, about 2 mg to about 9 mg per day based on mirdametinib free base, about 2.5 mg to about 8.5 mg per day based on mirdametinib free base, about 3 mg to about 8 mg per day based on mirdametinib free base, about 3.5 mg to about 7.5 mg per day based on mirdametinib free base, about 4 mg to about 7 mg per day based on mirdametinib free base, about 4.5 mg to about 6.5 mg per day based on mirdametinib free base, or about 5 mg to about 6 mg per day based on mirdametinib free base. In some aspects, the mirdametinib, or a pharmaceutically acceptable salt thereof, is administered in an amount of about 1 mg per day based on mirdametinib free base, about 1.5 mg per day based on mirdametinib free base, about 2 mg per day based on mirdametinib free base, about 2.5 mg per day based on mirdametinib free base, about 3 mg per day based on mirdametinib free base, about 3.5 mg per day based on mirdametinib free base, about 4 mg per day based on mirdametinib free base, about 4.5 mg per day based on mirdametinib free base, about 5 mg per day based on mirdametinib free base, about 5.5 mg per day based on mirdametinib free base, about 6 mg per day based on mirdametinib free base, about 6.5 mg per day based on mirdametinib free base, about 7 mg per day based on mirdametinib free base, about 7.5 mg per day based on mirdametinib free base, about 8 mg per day based on mirdametinib free base, about 8.5 mg per day based on mirdametinib free base, about 9 mg per day based on mirdametinib free base, about 9.5 mg per day based on mirdametinib free base, or about 10 mg per day based on mirdametinib free base.

In some aspects of any of the methods described herein, the mirdametinib, or a pharmaceutically acceptable salt thereof, is administered in a single dosage form comprising about 0.1 mg/m$^2$ to about 10 mg/m$^2$ based on mirdametinib free base, about 0.5 mg/m$^2$ to about 9.5 mg/m$^2$ based on mirdametinib free base, about 1 mg/m$^2$ to about 9 mg/m$^2$ based on mirdametinib free base, about 1.5 mg/m$^2$ to about 8.5 mg/m$^2$ based on mirdametinib free base, about 2 mg/m$^2$ to about 8 mg/m$^2$ based on mirdametinib free base, about 2.5 mg/m$^2$ to about 7.5 mg/m$^2$ based on mirdametinib free base, about 3 mg/m$^2$ to about 7 mg/m$^2$ based on mirdametinib free base, about 3.5 mg/m$^2$ to about 6.5 mg/m$^2$ based on mirdametinib free base, about 4 mg/m$^2$ to about 6 mg/m$^2$ based on mirdametinib free base, or about 4.5 mg/m$^2$ to about 5.5 mg/m$^2$ based on mirdametinib free base. In some aspects, the mirdametinib, or a pharmaceutically acceptable salt thereof, is administered in a single dosage form comprising about 0.1 mg/m$^2$ based on mirdametinib free base, about 0.2 mg/m$^2$ based on mirdametinib free base, about 0.3 mg/m$^2$ based on mirdametinib free base, about 0.4 mg/m$^2$ based on mirdametinib free base, about 0.5 mg/m$^2$ based on mirdametinib free base, about 1 mg/m$^2$ based on mirdametinib free base, about 1.5 mg/m$^2$ based on mirdametinib free base, about 2 mg/m$^2$ based on mirdametinib free base, about 2.5 mg/m$^2$ based on mirdametinib free base, about 3 mg/m$^2$ based on mirdametinib free base, about 3.5 mg/m$^2$ based on mirdametinib free base, about 4 mg/m$^2$ based on mirdametinib free base, about 4.5 mg/m$^2$ based on mirdametinib free base, about 5 mg/m$^2$ based on mirdametinib free base, about 5.5 mg/m$^2$ based on mirdametinib free base, about 6 mg/m$^2$ based on mirdametinib free base, about 6.5 mg/m$^2$ based on mirdametinib free base, about 7 mg/m$^2$ based on mirdametinib free base, about 7.5 mg/m$^2$ based on mirdametinib free base, about 8 mg/m$^2$ based on mirdametinib free base, about 8.5 mg/m² based on mirdametinib free base, about 9 mg/m² based on mirdametinib free base, about 9.5 mg/m² based on mirdametinib free base, or about 10 mg/m² based on mirdametinib free base.

In some aspects of any of the methods described herein, the mirdametinib, or a pharmaceutically acceptable salt thereof, is administered in a single dosage form comprising about 0.1 mg to about 10 mg based on mirdametinib free base, about 0.5 mg to about 9.5 mg based on mirdametinib free base, about 1 mg to about 9 mg based on mirdametinib free base, about 1.5 mg to about 8.5 mg based on mirdametinib free base, about 2 mg to about 8 mg based on mirdametinib free base, about 2.5 mg to about 7.5 mg based on mirdametinib free base, about 3 mg to about 7 mg based on mirdametinib free base, about 3.5 mg to about 6.5 mg based on mirdametinib free base, about 4 mg to about 6 mg based on mirdametinib free base, or about 4.5 mg to about 5.5 mg based on mirdametinib free base. In some aspects, the mirdametinib, or a pharmaceutically acceptable salt thereof, is administered in a single dosage form comprising about 0.1 mg based on mirdametinib free base, about 0.2 mg based on mirdametinib free base, about 0.3 mg based on mirdametinib free base, about 0.4 mg based on mirdametinib free base, about 0.5 mg based on mirdametinib free base, about 1 mg based on mirdametinib free base, about 1.5 mg based on mirdametinib free base, about 2 mg based on mirdametinib free base, about 2.5 mg based on mirdametinib free base, about 3 mg based on mirdametinib free base, about 3.5 mg based on mirdametinib free base, about 4 mg based on mirdametinib free base, about 4.5 mg based on mirdametinib free base, about 5 mg based on mirdametinib free base, about 5.5 mg based on mirdametinib free base, about 6 mg based on mirdametinib free base, about 6.5 mg based on mirdametinib free base, about 7 mg based on mirdametinib free base, about 7.5 mg based on mirdametinib free base, about 8 mg based on mirdametinib free base, about 8.5 mg based on mirdametinib free base, about 9 mg based on mirdametinib free base, about 9.5 mg based on mirdametinib free base, or about 10 mg based on mirdametinib free base.

In some aspects of any of the methods described herein, the mirdametinib, or a pharmaceutically acceptable salt thereof, is administered one, two, three, or four times per day. In some aspects, the mirdametinib, or a pharmaceutically acceptable salt thereof, is administered once daily. In some aspects, the mirdametinib, or a pharmaceutically acceptable salt thereof, is administered twice daily.

In some aspects of any of the methods described herein, the mirdametinib, or a pharmaceutically acceptable salt thereof, is administered twice daily in an amount of about 0.5 mg/m² to about 10 mg/m² based on mirdametinib free base, about 1 mg/m² to about 9.5 mg/m² based on mirdametinib free base, about 1.5 mg/m² to about 9 mg/m² based on mirdametinib free base, about 2 mg/m² to about 8.5 mg/m² based on mirdametinib free base, about 2.5 mg/m² to about 8 mg/m² based on mirdametinib free base, about 3 mg/m² to about 7.5 mg/m² based on mirdametinib free base, about 3.5 mg/m² to about 7 mg/m² based on mirdametinib free base, about 4 mg/m² to about 6.5 mg/m² based on mirdametinib free base, about 4.5 mg/m² to about 6 mg/m² based on mirdametinib free base, or about 5 mg/m² to about 6 mg/m² based on mirdametinib free base. In some aspects, the mirdametinib, or a pharmaceutically acceptable salt thereof, is administered twice daily in an amount of about 0.5 mg/m² based on mirdametinib free base, about 1 mg/m² based on mirdametinib free base, about 1.5 mg/m² based on mirdametinib free base, about 2 mg/m² based on mirdametinib free base, about 2.5 mg/m² based on mirdametinib free base, about 3 mg/m² based on mirdametinib free base, about 3.5 mg/m² based on mirdametinib free base, about 4 mg/m² based on mirdametinib free base, about 4.5 mg/m² based on mirdametinib free base, about 5 mg/m² based on mirdametinib free base, about 5.5 mg/m² based on mirdametinib free base, about 6 mg/m² based on mirdametinib free base, about 6.5 mg/m² based on mirdametinib free base, about 7 mg/m² based on mirdametinib free base, about 7.5 mg/m² based on mirdametinib free base, about 8 mg/m² based on mirdametinib free base, about 8.5 mg/m² based on mirdametinib free base, about 9 mg/m² based on mirdametinib free base, about 9.5 mg/m² based on mirdametinib free base, or about 10 mg/m² based on mirdametinib free base.

In some aspects of any of the methods described herein, the mirdametinib, or a pharmaceutically acceptable salt thereof, is administered twice daily in an amount of about 0.5 mg to about 10 mg based on mirdametinib free base, about 1 mg to about 9.5 mg based on mirdametinib free base, about 1.5 mg to about 9 mg based on mirdametinib free base, about 2 mg to about 8.5 mg based on mirdametinib free base, about 2.5 mg to about 8 mg based on mirdametinib free base, about 3 mg to about 7.5 mg based on mirdametinib free base, about 3.5 mg to about 7 mg based on mirdametinib free base, about 4 mg to about 6.5 mg based on mirdametinib free base, about 4.5 mg to about 6 mg based on mirdametinib free base, or about 5 mg to about 6 mg based on mirdametinib free base. In some aspects, the mirdametinib, or a pharmaceutically acceptable salt thereof, is administered twice daily in an amount of about 0.5 mg based on mirdametinib free base, about 1 mg based on mirdametinib free base, about 1.5 mg based on mirdametinib free base, about 2 mg based on mirdametinib free base, about 2.5 mg based on mirdametinib free base, about 3 mg based on mirdametinib free base, about 3.5 mg based on mirdametinib free base, about 4 mg based on mirdametinib free base, about 4.5 mg based on mirdametinib free base, about 5 mg based on mirdametinib free base, about 5.5 mg based on mirdametinib free base, about 6 mg based on mirdametinib free base, about 6.5 mg based on mirdametinib free base, about 7 mg based on mirdametinib free base, about 7.5 mg based on mirdametinib free base, about 8 mg based on mirdametinib free base, about 8.5 mg based on mirdametinib free base, about 9 mg based on mirdametinib free base, about 9.5 mg based on mirdametinib free base, or about 10 mg based on mirdametinib free base.

In some aspects of any of the methods described herein, the mirdametinib, or a pharmaceutically acceptable salt thereof, is administered in a total daily dose that does not exceed about 10 mg/m² based on mirdametinib free base, about 9.5 mg/m² based on mirdametinib free base, about 9 mg/m² based on mirdametinib free base, about 8.5 mg/m² based on mirdametinib free base, about 8 mg/m² based on mirdametinib free base, about 7.5 mg/m² based on mirdametinib free base, about 7 mg/m² based on mirdametinib free base, about 6.5 mg/m² based on mirdametinib free base, about 6 mg/m² based on mirdametinib free base, about 5.5 mg/m² based on mirdametinib free base, about 5 mg/m² based on mirdametinib free base, about 4.5 mg/m² based on mirdametinib free base, about 4 mg/m² based on mirdametinib free base, about 3.5 mg/m² based on mirdametinib free base, about 3 mg/m² based on mirdametinib free base, about 2.5 mg/m² based on mirdametinib free base, about 2 mg/m² based on mirdametinib free base, or about 1.5 mg/m² based on mirdametinib free base.

In some aspects of any of the methods described herein, the mirdametinib, or a pharmaceutically acceptable salt thereof, is administered in a total daily dose that does not exceed about 10 mg based on mirdametinib free base, about 9.5 mg based on mirdametinib free base, about 9 mg based on mirdametinib free base, about 8.5 mg based on mirdametinib free base, about 8 mg based on mirdametinib free base, about 7.5 mg based on mirdametinib free base, about 7 mg based on mirdametinib free base, about 6.5 mg based on mirdametinib free base, about 6 mg based on mirdametinib free base, about 5.5 mg based on mirdametinib free base, about 5 mg based on mirdametinib free base, about 4.5 mg based on mirdametinib free base, about 4 mg based on mirdametinib free base, about 3.5 mg based on mirdametinib free base, about 3 mg based on mirdametinib free base, about 2.5 mg based on mirdametinib free base, about 2 mg based on mirdametinib free base, or about 1.5 mg based on mirdametinib free base.

In some aspects of any of the methods described herein, the mirdametinib, or a pharmaceutically acceptable salt thereof, is administered as mirdametinib free base.

Methods for treating a tumor or cancer selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain, comprising administering to a patient in need thereof mirdametinib free base are provided herein.

In some aspects of any of the methods described herein, the tumor or cancer is plexiform neurofibromas. In some aspects, the tumor or cancer is plexiform neurofibromas associated with neurofibromatosis type 1.

In some aspects of any of the methods described herein, the tumor or cancer is high grade glioma. In some aspects, the high grade glioma is a primary cancer. In some aspects, the high grade glioma is a metastatic cancer.

In some aspects of any of the methods described herein, the tumor or cancer is low grade ovarian cancer.

In some aspects of any of the methods described herein, the tumor or cancer is Langerhans cell histiocytosis.

In some aspects of any of the methods described herein, the tumor or cancer is brain cancer.

In some aspects of any of the methods described herein, the tumor or cancer is a cancer that has metastasized to the patient's brain including lung cancer, breast cancer and melanoma.

In some aspects of any of the methods described herein, a therapeutically effective amount of mirdametinib free base is administered.

In some aspects of any of the methods described herein, the mirdametinib free base is administered in an amount of about 1 $mg/m^2$ to about 10 $mg/m^2$ per day, about 1.5 $mg/m^2$ to about 9.5 $mg/m^2$ per day, about 2 $mg/m^2$ to about 9 $mg/m^2$ per day, about 2.5 $mg/m^2$ to about 8.5 $mg/m^2$ per day, about 3 $mg/m^2$ to about 8 $mg/m^2$ per day, about 3.5 $mg/m^2$ to about 7.5 $mg/m^2$ per day, about 4 $mg/m^2$ to about 7 $mg/m^2$ per day, about 4.5 $mg/m^2$ to about 6.5 $mg/m^2$ per day, or about 5 $mg/m^2$ to about 6 $mg/m^2$ per day. In some aspects, the mirdametinib free base is administered in an amount of about 1 $mg/m^2$ per day, about 1.5 $mg/m^2$ per day, about 2 $mg/m^2$ per day, about 2.5 $mg/m^2$ per day, about 3 $mg/m^2$ per day, about 3.5 $mg/m^2$ per day, about 4 $mg/m^2$ per day, about 4.5 $mg/m^2$ per day, about 5 $mg/m^2$ per day, about 5.5 $mg/m^2$ per day, about 6 $mg/m^2$ per day, about 6.5 $mg/m^2$ per day, about 7 $mg/m^2$ per day, about 7.5 $mg/m^2$ per day, about 8 $mg/m^2$ per day, about 8.5 $mg/m^2$ per day, about 9 $mg/m^2$ per day, about 9.5 $mg/m^2$ per day, or about 10 $mg/m^2$ per day.

In some aspects of any of the methods described herein, the mirdametinib free base is administered in an amount of about 1 mg to about 10 mg per day, about 1.5 mg to about 9.5 mg per day, about 2 mg to about 9 mg per day, about 2.5 mg to about 8.5 mg per day, about 3 mg to about 8 mg per day, about 3.5 mg to about 7.5 mg per day, about 4 mg to about 7 mg per day, about 4.5 mg to about 6.5 mg per day, or about 5 mg to about 6 mg per day. In some aspects, the mirdametinib free base is administered in an amount of about 1 mg per day, about 1.5 mg per day, about 2 mg per day, about 2.5 mg per day, about 3 mg per day, about 3.5 mg per day, about 4 mg per day, about 4.5 mg per day, about 5 mg per day, about 5.5 mg per day, about 6 mg per day, about 6.5 mg per day, about 7 mg per day, about 7.5 mg per day, about 8 mg per day, about 8.5 mg per day, about 9 mg per day, about 9.5 mg per day, or about 10 mg per day.

In some aspects of any of the methods described herein, the mirdametinib free base is administered in a single dosage form comprising about 0.1 $mg/m^2$ to about 10 $mg/m^2$, about 0.5 $mg/m^2$ to about 9.5 $mg/m^2$, about 1 $mg/m^2$ to about 9 $mg/m^2$, about 1.5 $mg/m^2$ to about 8.5 $mg/m^2$, about 2 $mg/m^2$ to about 8 $mg/m^2$, about 2.5 $mg/m^2$ to about 7.5 $mg/m^2$, about 3 $mg/m^2$ to about 7 $mg/m^2$, about 3.5 $mg/m^2$ to about 6.5 $mg/m^2$, about 4 $mg/m^2$ to about 6 $mg/m^2$, or about 4.5 $mg/m^2$ to about 5.5 $mg/m^2$. In some aspects, the mirdametinib free base is administered in a single dosage form comprising about 0.1 $mg/m^2$, about 0.2 $mg/m^2$, about 0.3 $mg/m^2$, about 0.4 $mg/m^2$, about 0.5 $mg/m^2$, about 1 $mg/m^2$, about 1.5 $mg/m^2$, about 2 $mg/m^2$, about 2.5 $mg/m^2$, about 3 $mg/m^2$, about 3.5 $mg/m^2$, about 4 $mg/m^2$, about 4.5 $mg/m^2$, about 5 $mg/m^2$, about 5.5 $mg/m^2$, about 6 $mg/m^2$, about 6.5 $mg/m^2$, about 7 $mg/m^2$, about 7.5 $mg/m^2$, about 8 $mg/m^2$, about 8.5 $mg/m^2$, about 9 $mg/m^2$, about 9.5 $mg/m^2$, or about 10 $mg/m^2$.

In some aspects of any of the methods described herein, the mirdametinib free base is administered in a single dosage form comprising about 0.1 mg to about 10 mg, about 0.5 mg to about 9.5 mg, about 1 mg to about 9 mg, about 1.5 mg to about 8.5 mg, about 2 mg to about 8 mg, about 2.5 mg to about 7.5 mg, about 3 mg to about 7 mg, about 3.5 mg to about 6.5 mg, about 4 mg to about 6 mg, or about 4.5 mg to about 5.5 mg. In some aspects, the mirdametinib free base is administered in a single dosage form comprising about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

In some aspects of any of the methods described herein, the mirdametinib free base is administered one, two, three, or four times per day. In some aspects, the mirdametinib free base is administered once daily. In some aspects, the mirdametinib free base is administered twice daily.

In some aspects of any of the methods described herein, the mirdametinib free base is administered twice daily in an amount of about 0.5 $mg/m^2$ to about 10 $mg/m^2$, about 1 $mg/m^2$ to about 9.5 $mg/m^2$, about 1.5 $mg/m^2$ to about 9 $mg/m^2$, about 2 $mg/m^2$ to about 8.5 $mg/m^2$, about 2.5 $mg/m^2$ to about 8 $mg/m^2$, about 3 $mg/m^2$ to about 7.5 $mg/m^2$, about 3.5 $mg/m^2$ to about 7 $mg/m^2$, about 4 $mg/m^2$ to about 6.5 $mg/m^2$, about 4.5 $mg/m^2$ to about 6 $mg/m^2$, or about 5 $mg/m^2$ to about 6 $mg/m^2$. In some aspects, the mirdametinib free base is administered twice daily in an amount of about 0.5 $mg/m^2$, about 1 $mg/m^2$, about 1.5 $mg/m^2$, about 2 $mg/m^2$, about 2.5 $mg/m^2$, about 3 $mg/m^2$, about 3.5 $mg/m^2$, about 4 $mg/m^2$, about 4.5 $mg/m^2$, about 5 $mg/m^2$, about 5.5 mg/m², about 6 mg/m², about 6.5 mg/m², about 7 mg/m², about 7.5 mg/m², about 8 mg/m², about 8.5 mg/m², about 9 mg/m², about 9.5 mg/m², or about 10 mg/m².

In some aspects of any of the methods described herein, the mirdametinib free base is administered twice daily in an amount of about 0.5 mg to about 10 mg, about 1 mg to about 9.5 mg, about 1.5 mg to about 9 mg, about 2 mg to about 8.5 mg, about 2.5 mg to about 8 mg, about 3 mg to about 7.5 mg, about 3.5 mg to about 7 mg, about 4 mg to about 6.5 mg, about 4.5 mg to about 6 mg, or about 5 mg to about 6 mg. In some aspects, the mirdametinib free base is administered twice daily in an amount of about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

In some aspects of any of the methods described herein, the mirdametinib free base is administered in a total daily dose that does not exceed about 10 mg/m², about 9.5 mg/m², about 9 mg/m², about 8.5 mg/m², about 8 mg/m², about 7.5 mg/m², about 7 mg/m², about 6.5 mg/m², about 6 mg/m², about 5.5 mg/m², about 5 mg/m², about 4.5 mg/m², about 4 mg/m², about 3.5 mg/m², about 3 mg/m², about 2.5 mg/m², about 2 mg/m², or about 1.5 mg/m².

In some aspects of any of the methods described herein, the mirdametinib free base is administered in a total daily dose that does not exceed about 10 mg, about 9.5 mg, about 9 mg, about 8.5 mg, about 8 mg, about 7.5 mg, about 7 mg, about 6.5 mg, about 6 mg, about 5.5 mg, about 5 mg, about 4.5 mg, about 4 mg, about 3.5 mg, about 3 mg, about 2.5 mg, about 2 mg, or about 1.5 mg.

In some aspects of any of the methods described herein, the mirdametinib, or a pharmaceutically acceptable salt thereof, exhibits high blood-brain-barrier penetration.

In some aspects of any of the methods described herein, the patient is a human.

In some aspects of any of the methods described herein, the human has an age of ≥2 and <25 years. In some aspects, the human has an age of ≥2 and 18 years.

In some aspects of any of the methods described herein, the human has had no prior exposure to MEK inhibitors. In some aspects, the human has not responded to prior treatment to one or more MEK inhibitors.

In some aspects of any of the methods described herein, the mirdametinib, or a pharmaceutically acceptable salt thereof, is administered orally. In some aspects, the mirdametinib, or a pharmaceutically acceptable salt thereof, is administered orally as a solid dosage form. In some aspects, the solid dosage form is a tablet or capsule. In some aspects, the solid dosage form is a capsule. In some aspects, the mirdametinib, or a pharmaceutically acceptable salt thereof, is dispersible in a potable liquid or orodispersible in a patient's saliva.

In some aspects of any of the methods described herein, the mirdametinib, or a pharmaceutically acceptable salt thereof, is administered as a monotherapy to treat the tumor or cancer.

In some aspects of any of the methods described herein, the mirdametinib, or a pharmaceutically acceptable salt thereof, is administered in combination with another active ingredient and/or surgery to treat the tumor or cancer.

EXAMPLE

Example 1

Mirdametinib free base (Lots #1, 2, and 3) having the properties in the table below were prepared.

| Property | Drug Substance Lot 1 | Drug Substance Lot 2 | Drug Substance Lot 3 |
|---|---|---|---|
| $D_{10}$ (μm) | 4.9 | 7.6 | 17.8 |
| $D_{50}$ (μm) | 20.9 | 28.4 | 46.5 |
| $D_{90}$ (μm) | 101.5 | 120.7 | 217.1 |
| Bulk density (g/mL) | 0.169 | 0.197 | — |
| Tap density (g/mL) | 0.394 | 0.434 | — |
| Carr's Index | 57.1 | 54.6 | — |

1 and 2 mg capsules having the formulations described in the table below were prepared using one of Lots #1 and 2 from Example 1. The ingredients were mixed and subject to roller compaction prior to being encapsulated in capsule shells (size 3, opaque hard gelatin capsules).

| | | 1 mg Capsule | | 2 mg Capsule | |
|---|---|---|---|---|---|
| Ingredient | Function | % w/w | mg/capsule | % w/w | mg/capsule |
| Mirdametinib | Active ingredient | 0.77 | 1.0 | 0.77 | 2.0 |
| Microcrystalline Cellulose | Diluent | 93.23 | 121.2 | 93.23 | 242.4 |
| Croscarmellose Sodium | Disintegrant | 5.00 | 6.5 | 5.00 | 13.0 |
| Magnesium Stearate | Lubricant | 1.00 | 1.3 | 1.00 | 2.6 |
| Total | | 100 | 130.0 | 100 | 260.0 |

The dissolution of the 1 mg and 2 mg capsules prepared with mirdametinib from Lots #1 and #2 were measured according to the USP basket method in 0.1 N HCl (0.1 N HCL aqueous solution) and at 75 rpm, and are shown in FIG. 1. As shown, the tested capsules released greater than 80% of the mirdametinib within 15 minutes.

Figure 2:
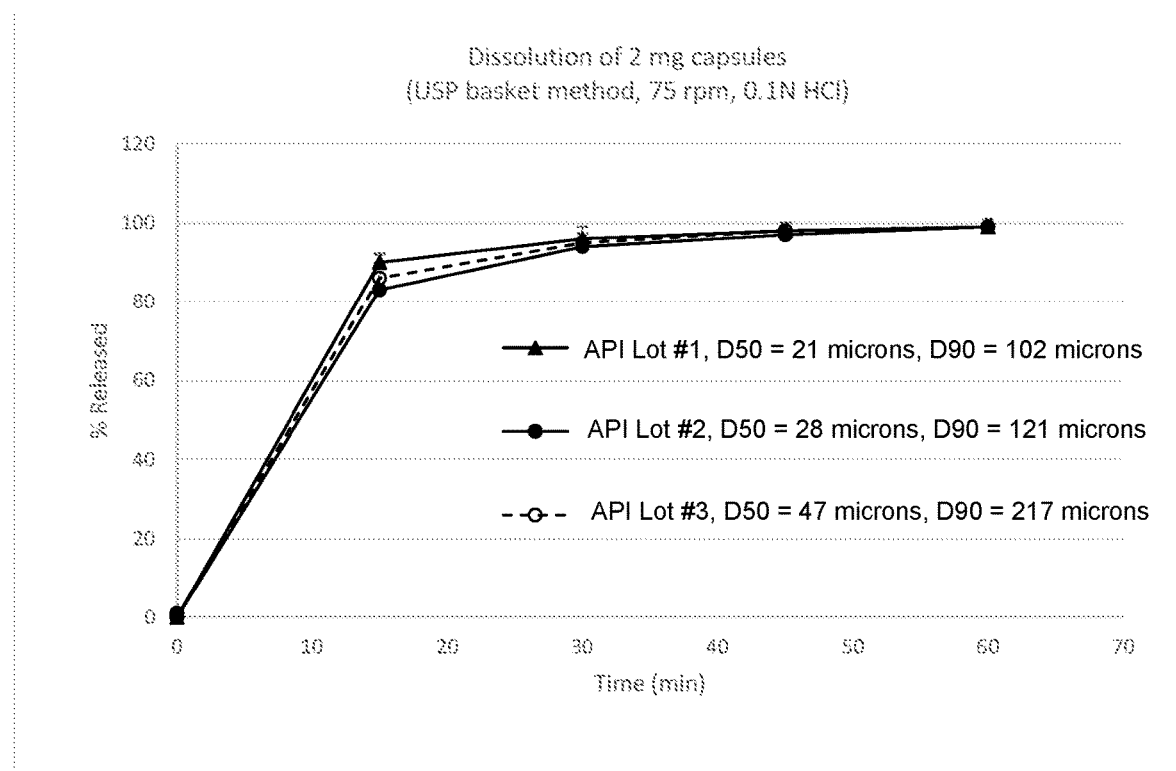
FIG. 2 is a graph showing the release of mirdametinib according to the USP basket method in 0.1 N HCl and at 75 rpm from 2 mg capsules prepared with mirdametinib from Lots #1, 2, and 3 as described in Example 2.

2 mg capsules having the formulation provided above were prepared from Lot #3. The dissolution of the 2 mg capsules prepared from Lots #1, 2, and 3 were measured according to the USP basket method in 0.1 N HCl and at 75 rpm, and are shown in FIG. 2. As shown, the tested capsules released greater than 80% of the mirdametinib within 15 minutes.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed:

1. An oral dosage form comprising (a) mirdametinib having a d90 no more than 250 microns and (b) one or more pharmaceutically acceptable excipients.

2. The oral dosage form of claim 1, wherein the mirdametinib has a d50 of no more than 50 microns.

3. The oral dosage form of claim 1, wherein the mirdametinib has a d50 of no more than 30 microns.

4. The oral dosage form of claim 1, wherein the dosage form is a capsule prepared by (i) roller compaction of a blend of the mirdametinib and one or more pharmaceutically acceptable excipients and (ii) encapsulating the compacted blend into a capsule.

5. An oral dosage form comprising (a) 1 mg mirdametinib having a d90 no more than 250 microns and (b) one or more pharmaceutically acceptable excipients, wherein the dosage form provides upon oral administration, on the first day of treatment with mirdametinib, an $AUC_{0-12h}$ less than 400 ng·h/mL, a $C_{max}$ no more than 40 ng/ml, or both.

6. The oral dosage form of claim 5, wherein the dosage form provides upon oral administration, on the first day of treatment with mirdametinib, an $AUC_{0-12h}$ less than 200 ng·h/mL.

7. The oral dosage form of claim 5, wherein the dosage form provides upon oral administration, on the first day of treatment with mirdametinib, $AUC_{0-12h}$ less than 100 ng·h/mL.

8. The oral dosage form of claim 5, wherein the dosage form provides upon oral administration, on the first day of treatment with mirdametinib, a $C_{max}$ no more than 32 ng/mL.

9. The oral dosage form of claim 5, wherein the dosage form provides upon oral administration, on the first day of treatment with mirdametinib, a $C_{max}$ no more than 30 ng/mL.

10. The oral dosage form of claim 1, wherein the dosage form is a capsule.

11. The oral dosage form of claim 1, wherein the dosage form is a tablet.

12. The oral dosage form of claim 11, wherein the dosage form is a dispersible tablet.

13. A method of treating a human patient who has neurofibromatosis type 1 (NF1) associated inoperable plexiform neurofibromas (PN) comprising orally administering an effective amount of one or more oral dosage forms of claim 1 to the patient.

14. The method of claim 13, wherein about 2 mg/m² mirdametinib is administered to the patient twice daily.

15. The method of claim 13, wherein
(a) for a patient having a body surface area no more than 0.69 m², the patient is initially administered 1 mg mirdametinib twice daily,
(b) for a patient having a body surface area of 0.7 to 1.04 m², the patient is initially administered 2 mg mirdametinib twice daily,
(c) for a patient having a body surface area of 1.05 to 1.49 m², the patient is initially administered 3 mg mirdametinib twice daily, and
(d) for a patient having a body surface area of at least 1.5 m², the patient is initially administered 4 mg mirdametinib twice daily.

16. The method of claim 13, wherein
(a) for a patient having a body surface area of 0.4 to 0.59 m², the patient is initially administered 1 mg mirdametinib twice daily,
(b) for a patient having a body surface area of 0.6 to 0.79 m², the patient is initially administered 1.5 mg mirdametinib twice daily,
(c) for a patient having a body surface area of 0.8 to 0.99 m², the patient is initially administered 2 mg mirdametinib twice daily,
(d) for a patient having a body surface area of 1.0 to 1.19 m², the patient is initially administered 2.5 mg mirdametinib twice daily,
(e) for a patient having a body surface area of 1.2 to 1.39 m², the patient is initially administered 3 mg mirdametinib twice daily,
(f) for a patient having a body surface area of 1.4 to 1.59 m², the patient is initially administered 3.5 mg mirdametinib twice daily, and
(g) for a patient having a body surface area of at least 1.6 m², the patient is initially administered 4 mg mirdametinib twice daily.

17. The method of claim 16, wherein the patient is less than 12 years of age.

18. The method of claim 16, wherein the mirdametinib is administered in the form of one or more 0.5 mg tablets, one or more 1 mg tablets, or any combination of any of the foregoing.

19. The method of claim 16, wherein the mirdametinib is administered in the form of one or more dispersible tablets.

20. The method of claim 13, wherein
(a) for a patient having a body surface area of 0.4 to 0.69 m², the patient is initially administered 1 mg mirdametinib twice daily,
(b) for a patient having a body surface area of 0.7 to 1.04 m², the patient is initially administered 2 mg mirdametinib twice daily,
(c) for a patient having a body surface area of 1.05 to 1.49 m², the patient is initially administered 3 mg mirdametinib twice daily, and
(d) for a patient having a body surface area of at least 1.5 m², the patient is initially administered 4 mg mirdametinib twice daily.

21. The method of claim 20, wherein the patient is at least 12 years of age.

22. The method of claim 20, wherein the mirdametinib is administered in the form of one or more capsules.

23. The method of claim 13, wherein
(a) for a patient having a body surface area of 0.4 to 0.59 m², the patient is initially administered 1 mg mirdametinib twice daily,
(b) for a patient having a body surface area of 0.6 to 0.79 m², the patient is initially administered 1.5 mg mirdametinib twice daily,
(c) for a patient having a body surface area of 0.8 to 0.99 m², the patient is initially administered 2 mg mirdametinib twice daily,
(d) for a patient having a body surface area of 1.0 to 1.39 m², the patient is initially administered 2.5 mg mirdametinib twice daily,
(e) for a patient having a body surface area of 1.4 to 1.59 m², the patient is initially administered 3 mg mirdametinib twice daily,
(f) for a patient having a body surface area of 1.6 to 1.69 m², the patient is initially administered 3.5 mg mirdametinib twice daily, and
(g) for a patient having a body surface area of at least 1.7 m², the patient is initially administered 4 mg mirdametinib twice daily.

24. The method of claim 23, wherein the patient is less than 12 years of age.

25. The method of claim 23, wherein the mirdametinib is administered in the form of one or more 0.5 mg tablets, one or more 1 mg tablets, or any combination of any of the foregoing.

26. The method of claim 23, wherein the mirdametinib is administered in the form of one or more dispersible tablets.

27. The method of claim 13, wherein the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis.

28. The method of claim 27, wherein in step (i), mirdametinib is selected based on a response rate of at least 70%.

29. The method of claim 13, wherein the mirdametinib is in the form of one or more dispersible tablets, and prior to administration, the one or more dispersible tablets are dispersed in water to form a suspension and optionally the suspension is swirled until no lumps remain.

30. The method of claim 13, wherein each of the one or more oral dosage forms is a capsule prepared by (i) roller compaction of a blend of the mirdametinib and one or more pharmaceutically acceptable excipients and (ii) encapsulating the compacted blend into a capsule.

* * * * *